United States Patent [19]

Handte

[11] 4,263,440

[45] Apr. 21, 1981

[54] 2-BENZAZOLYL, 2-BENZOTHIAZOLYL AND 2-IMIDAZOLYL

[75] Inventor: Reinhard Handte, Hofheim am Taunus, Fed. Rep. of Germany

[73] Assignee: Hoechst Aktiengesellschaft, Frankfurt am Main, Fed. Rep. of Germany

[21] Appl. No.: 937,092

[22] Filed: Aug. 28, 1978

[30] Foreign Application Priority Data

Aug. 30, 1977 [DE] Fed. Rep. of Germany ....... 2738963

[51] Int. Cl.³ ................. C07D 277/68; C07D 263/58; C07D 235/26
[52] U.S. Cl. .................................. 548/165; 548/169; 548/221; 71/90; 71/92; 71/88
[58] Field of Search ...................... 260/304 B, 307 D; 548/165, 169, 221

[56] References Cited

U.S. PATENT DOCUMENTS

| | | | |
|---|---|---|---|
| 2,541,003 | 2/1951 | Day et al. | 260/304 B |
| 3,004,034 | 10/1961 | D'Amico | 260/304 B |
| 3,658,835 | 4/1972 | Gates et al. | 260/304 B |

FOREIGN PATENT DOCUMENTS 2738963 7/1979 Fed. Rep. of Germany ........... 548/169

OTHER PUBLICATIONS

Cossey et al., J. Chem. Soc., pp. 954 to 973 (1965).

Primary Examiner—Donald G. Daus
Assistant Examiner—W. B. Springer
Attorney, Agent, or Firm—Curtis, Morris & Safford

[57] ABSTRACT

Heterocyclic phenyl ethers of the formula

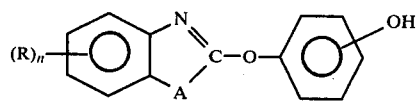

in which $(R)_n$ is hydrogen or up to three identical or different substituents selected from halogen, $CF_3$, $NO_2$, CN, alkyl, alkoxy and alkylthio, and A is oxygen, sulfur or $N(C_1-C_4)$alkyl, provided that the —OH group is not in para-position if $(R)_n$ is hydrogen and A is sulfur, are useful as starting materials for the manufacture of selective herbicides.

1 Claim, No Drawings

2-BENZAZOLYL, 2-BENZOTHIAZOLYL AND 2-IMIDAZOLYL

J.Chem.Soc. 1965, pages 954 to 73 describes the compound 4-(benzthiazolyl-2'-oxy)-phenol and its manufacture from 2-chloro-benzthiazole and hydroquinone in boiling ethanol in the presence of metallic sodium. Nothing is said about the utility of this compound.

It is an object of this invention to provide heterocyclic phenyl ethers of the general formula I

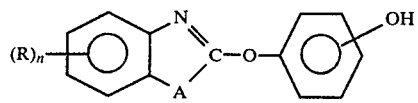

in which
R denotes identical or different radicals selected from the group of halogen, $CF_3$, $NO_2$, $CN$, $(C_1-C_4)$alkyl, $(C_1-C_4)$alkoxy, $(C_1-C_4)$alkylthio,
A is O, S, or N-$(C_1-C_4)$alkyl and
n is zero to 3,
with the proviso that if n is zero and A is S the free OH group does not stand in p-position to the ether linkage.

The compounds of formula I are useful as starting materials for effective biocides, in particular herbicides.

Preferred compounds of formula I for the above purpose are those in which n is zero or if n is not zero, those in which R is halogen, $CF_3$, $NO_2$ or methyl, preferred halogens being fluorine, chlorine and/or bromine.

It is another object of the invention to provide a process for the manufacture of compounds of formula I, which comprises reacting
(a) compounds of formula II

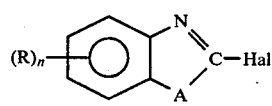

in which Hal is halogen, preferably chlorine or bromine, or
(b) compounds of formula IV

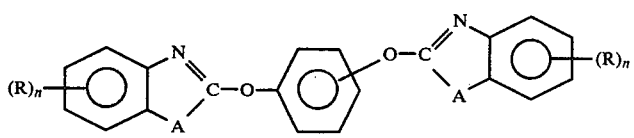

with compounds of formula III

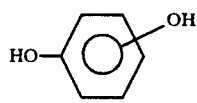

in the presence of basic compounds.

The compounds of formula II can be prepared by known processes, for example from corresponding 2-mercapto- or 2-oxo-substituted compounds by halogenation or from the 2-amino-substituted compounds by diazotization with subsequent Sandmeyer reaction (cf. for example C.A. 59, 396 j; Am.Chem.J. 21, 11 (1899)).

The compounds of formula IV can be prepared by process (a) by reacting at least 2 mols of compound II with 1 mol of compound III.

Suitable compounds of formula II are the 2-halogeno-compounds of correspondingly substituted benzthiazoles, benzoxazoles and 1-alkyl-benzimidazoles, for example
2-chloro-benzthiazole, -benzoxazole, -1-methyl-benzimidazole,
2-chloro-6-fluoro-benzthiazole, -benzoxazole, 1-methyl-benzimidazole,
2,6-dichloro-benzthiazole, -benzoxazole, -1-butyl-benzimidazole,
2,5-dichloro-benzthiazole, -benzoxazole, -1-methyl-benzimidazole,
2-chloro-5-methyl-benzthiazole, -benzoxazole, -1-methyl-benzimidazole,
2-chloro-6-methyl-benzthiazole, -benzoxazole, -1-methyl-benzimidazole,
2-chloro-6-ethyl-benzthiazole, -benzoxazole, -1-methyl-benzimidazole,
2-chloro-6-nitro-benzthiazole, -benzoxazole, -1-methyl-benzimidazole,
2,5-dichloro-6-nitro-benzthiazole, -benzoxazole, -1-methyl-benzimidazole,
2-chloro-5-methoxy-benzthiazole, -benzoxazole, -1-methyl-benzimidazole,
2-chloro-6-methoxy-benzthiazole, -benzoxazole, -1-methyl-benzimidazole,
2-chloro-6-methylthio-benzthiazole, -benzoxazole, -1-methyl-benzimidazole,
2,5,6-trichloro-benzthiazole, -benzoxazole, -1-methyl-benzimidazole,
2-chloro-5-bromo-benzthiazole, -benzoxazole, -1-methyl-benzimidazole,
2-chloro-6-bromo-benzthiazole, -benzoxazole, -1-methyl-benzimidazole,
2-chloro-5,6-dibromo-benzthiazole, -benzoxazole, -1-methyl-benzimidazole,
2-chloro-5-trifluoromethyl-benzthiazole, -benzoxazole, -1-methyl-benzimidazole,
2-chloro-6-trifluoromethyl-benzthiazole, -benzoxazole, -1-methyl-benzimidazole,
2-chloro-6-cyano-benzthiazole, -benzoxazole, -1-methyl-benzimidazole, and the corresponding 2-bromo-derivatives.

The reaction temperatures are in the range between preferably 90° and 150° C., optionally at the boiling point of the solvent used. In process (a) temperatures below 80° C. lead to the formation of increasing amounts of compound IV as undesired by-product. At temperatures above 80° C., however, this by-product reacts with further amounts of compound III to give compound I (cf. process b).

The reaction can also be carried out at a temperature above boiling point of the solvent used in a closed vessel under inherent pressure. This is necessary if the solvent used has a boiling point below 80° C.

Preferably, polar aprotic solvents are used, for example acid amides such as dimethyl formamide, dimethyl acetamide, diethyl acetamide, N-methylpyrrolidone and hexamethyl-phosphoric acid triamide; dimethyl sulfoxide, nitriles such as acetonitrile or propionitrile; ketones such as acetone, methylethylketone or methylisobutylketone. Aliphatic alcohols and aromatic hydrocarbons such as toluene or xylene may also be used.

Suitable basic compounds are the usual organic and inorganic bases, for example tertiary amines such as pyridine or triethylamine-, alcoholates such as sodium and potassium methylate, ethylate or butylate; preferably, however, inorganic bases such as potassium or sodium hydroxide or the corresponding carbonates. They are used in at least stoichiometric and preferably in at least equimolar amounts or in an excess of 10 to 20% thereabove. Larger amounts may also be used, but they do not offer any advantage and result in an increased salt load.

The molar ratio II:III or IV:III of the reactants can be varied within wide limits. Compound III can be used, for example in twice the molar amount or more, relative to compound II. Since the removal of unreacted compound III requires additional operations which may lead to yield losses, it is preferred, however, to use about equimolar amounts or an excess of at maximum 5 to 10% of compound III. Working with approximately equimolar amounts has the additional advantage that the reaction products can be reacted further without purification.

To carry out process (a) a mixture of compound III and the basic compound in a suitable solvent is generally heated to reaction temperature whereby the salt of compound III is formed at least partially. Compound II, optionally dissolved in the same solvent, is then added and the mixture is stirred at elevated temperature until the reaction is complete. It is likewise possible to prepare first the salt (monosalt) of compound III, which is then reacted with compound II. The addition of the reactants in another order of succession is also possible. The required reaction time depends on the reaction temperature, the solvent used and the ratio of II:III and decreases with increasing temperature and increasing excess of compound III. In general, the reaction is complete after 30 minutes to 50 hours.

Process (b) is carried out in a manner analogous to (a) using, instead of a compound II, compound IV which can be prepared from II and III. The bases used in this reaction serve for the preparation of the salts of compounds III, which then react with the bis-ethers of formula IV to yield compounds (salts) of formula I.

Both reactions are preferably carried out under a protective gas such as, for example, $N_2$, Ar, $CO_2$, preferably $N_2$.

When the reaction is complete, the reaction mixture is acidified, the salt formed is filtered off and the solvent is distilled off, optionally after a water wash. When working with an excess of compound III, the latter is removed by taking up the reaction mixture in a solvent immiscible with water, for example hot xylene, repeatedly washing with a small amount of hot water, drying the organic phase and distilling off the solvent.

Further processing methods are described in the examples.

The compounds I obtained in this manner can be further purified by recrystallization, distillation or reprecipitation, but in many cases their purity is sufficient for further reactions.

Processes (a) and (b) can also be used with advantage for the reaction of 2-halogeno-, especially 2-chlorobenzthiazole with hydroquinone.

As already mentioned, the compounds of formula I are useful as starting materials for herbicides, in particular those proposed in German Offenlegungsschrift 2,640,730. According to this specification valuable selective herbicides are obtained by reacting in known manner compounds of the formula I with 2-halopropionic acid derivatives such as esters and amides. For example 2-[4'-(6''-chlorobenzthiazolyl-2''-oxy)-phenoxy]-propionic acid ethyl ester can be manufactured from 4-(6'-chlorobenzthiazolyl-2'-oxy)phenol and 2-bromopropionic acid ethyl ester in the presence of potassium carbonate.

The following examples illustrate the invention.

EXAMPLE 1

4-(6'-chlorobenzthiazolyl-2'-oxy)-phenol

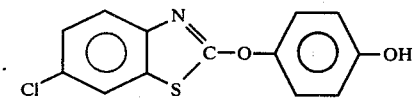

A mixture of 12.1 g (0.11 mol) of hydroquinone, 16.6 g (0.12 mol) of potassium carbonate and 120 ml of dimethyl acetamide was stirred for 1.5 hours at 95° to 100° C. under nitrogen as protective gas. 20.4 g (0.1 mol) of 2,6-dichlorobenzthiazole, dissolved in 50 cc of dimethyl acetamide were then added dropwise over a period of 30 minutes. After the addition, the temperature was maintained at 95° to 100° C. and the course of the reaction was observed by thin layer chromatography. After a reaction time of 6 hours, the conversion was about 90 to 95%. To complete the reaction the above temperature was maintained for 16 hours altogether. The salt was filtered off and the filtrate was added, while stirring, to about 500 cc of ice water. A pH of 2 was then adjusted with 10% sulfuric acid, the light precipitate was filtered off with suction, washed neutral with water and dried. 27 g (97.2% of the theory) of 4-(6'-chlorobenzthiazolyl-2'-oxy)-phenol were obtained, m.p. 177°–178° C. (from xylene)

Similar results were obtained by using, under otherwise the same reaction conditions, N-methylpyrrolidone, methylisobutylketone, acetonitrile, methylethylketone, acetone or ethanol (with sodium ethylate instead of $K_2CO_3$ as base) instead of dimethyl acetamide.

EXAMPLE 2

4-(5'-chlorobenzoxazolyl-2'-oxy)-phenol

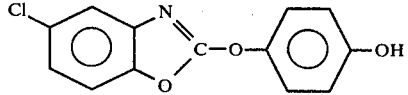

110 g (1 mol) of hydroquinone and 82.8 g (0.6 mol) of potassium carbonate in 600 ml of dimethyl formamide were stirred for 1½ hours at 120° C. under nitrogen as protective gas. 94 g (0.5 mol) of 2,5-dichlorobenzoxazole in 150 ml of dimethyl formamide, dissolved at 95° C., were then added dropwise over a period of 1½ hours. After the addition, the temperature was maintained. The reaction was complete ½ hour after the addition. By thin layer chromatography only 5'-chlorobenzoxazolyloxy-phenol and hydroquinone could be detected and no 2,5-dichlorobenzoxazole. The salt portion was filtered off and the filtrate was added, while stirring, to about 2 liters of ice water. A pH of 2 was adjusted with 10% sulfuric acid and the light precipitate was filtered off with suction, washed neutral with water and dried. The reaction product was then taken up in hot xylene and repeatedly washed with hot water to remove excess hydroquinone. Cooling of the xylene phase and suction filtration of the precipitate yielded 106.8 g (81.7% of theory) of 4-(5'-chlorobenzoxazolyl-2'-oxy)-phenol, m.p. 179.5° to 181° C.

EXAMPLE 3

4-(5'-chlorobenzthiazolyl-2'-oxy)-phenol

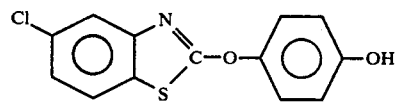

22 g (0.2 mol) of hydroquinone and 16.6 g (0.12 mol) of potassium carbonate in 120 cc of dimethylsulfoxyde were stirred for 1 hour at 120° C. under nitrogen as protective gas. 20.4 g (0.1 mol) of 2,5-dichlorobenz-thiazole dissolved in 50 ml of dimethylsulfoxide were added dropwise over a period of 1 hour. After the addition, the temperature was maintained for 2½ hours. After that time only 5'-chlorobenzthiazolyloxy-phenol and hydroquinone and no 2,5-dichlorobenzthiazole could be detected by thin-layer chromatography. The salt precipitate was filtered off and the filtrate added, while stirring, to about 500 cc of icewater. A pH of 2 was adjusted with 10% sulfuric acid and the light precipitate was filtered off with suction, washed neutral with water and dried. After drying, the reaction product was taken up in hot xylene and repeatedly washed with hot water to remove the excess amount of hydroquinone. After cooling of the xylene phase and suction filtration, 23 g (82.7% of the theory) of 4-(5'-chlorobenzthiazolyl-2'-oxy)-phenol, m.p. 189° to 190° C., were obtained.

EXAMPLE 4

4-(6'-chlorobenzthiazolyl-2'-oxy)-phenol

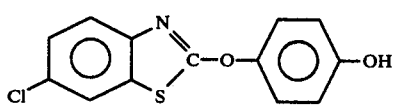

12.1 g (0.11 mol) of hydroquinone and 16.6 g (0.12 mol) of potassium carbonate in 150 cc of dimethyl formamide were stirred for 1½ hours at 10° C. under nitrogen as protective gas. After the addition of 44.5 g (0.1 mol) of hydroquinone-1,4-bis-6'chlorobenzthiazolyl-2'-ether the temperature was maintained. The splitting of the bis-ether was followed by thin-layer chromatography. The reaction was complete after 8 hours. After cooling, the reaction mixture was stirred into 500 cc of icewater. A pH of 2 was adjusted with 10% sulfuric acid and the light precipitate filtered off with suction, washed neutral with water and dried. 50.4 g (91% of the theory) of 4-(6'-chlorobenzthiazolyl-2'-oxy)-phenol, m.p. 175° C. were obtained. The product obtained after recrystallization from xylene has a melting point of 177° to 178° C.

According to Examples 1 to 4 the following compounds were prepared:

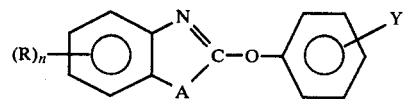

| Example No. | $(R)_n$ | A | Y | m.p. (°C.) |
|---|---|---|---|---|
| 5 | 5-$CH_3$ | S | 4-OH | 165.5–166 |
| 6 | 6-$CH_3$ | S | 4-OH | 152–152.5 |
| 7 | 6-$NO_2$ | S | 4-OH | |
| 8 | 6-$NO_2$ | S | 3-OH | 172 |
| 9 | 5-$CH_3O$ | S | 2-OH | |
| 10 | H | S | 3-OH | 146–147 |
| 11 | 6-$CH_3O$ | S | 4-OH | |
| 12 | H | S | 2-OH | 155 |
| 13 | 5-Cl | S | 3-OH | |
| 14 | 5-Cl | S | 2-OH | |
| 15 | 6-Cl | S | 3-OH | |
| 16 | 6-Cl | S | 2-OH | |
| 17 | 6-$NO_2$ | S | 2-OH | |
| 18 | 5-Br | S | 3-OH | |
| 19 | 6-Br | S | 4-OH | |
| 20 | 5-Br | S | 4-OH | 183.5–184 |
| 21 | H | N-$CH_3$ | 4-OH | 203 |
| 22 | H | O | 3-OH | |
| 23 | H | O | 4-OH | 145–146 |
| 24 | H | O | 2-OH | |
| 25 | H | N-$CH_3$ | 3-OH | 209 |
| 26 | 5-$CF_3$ | S | 4-OH | |
| 27 | 5-Cl | O | 4-OH | 179.5–180 |
| 28 | 5-Cl | O | 3-OH | |
| 29 | 5-Cl | O | 2-OH | |
| 30 | 6-Cl | O | 3-OH | |
| 31 | 6-Cl | O | 2-OH | |
| 32 | 6-Cl | O | 4-OH | 183.5–184 |
| 33 | 6-$NO_3$ | O | 4-OH | |
| 34 | 6-$NO_2$ | O | 3-OH | |
| 35 | H | N-$CH_3$ | 2-OH | 199.5 |
| 36 | 5,6-di-Cl | S | 4-OH | |
| 37 | 5-Cl,6-$CH_3$ | S | 4-OH | 149–150.5 |
| 38 | 5,6-di-$CH_3$ | S | 4-OH | 171–171.5 |
| 39 | 6-$C_2H_5O$ | S | 4-OH | 139 |
| 40 | 7-Cl | S | 4-OH | 143.5–144 |

What is claimed is:
1. A heterocyclic phenyl ether of the formula I

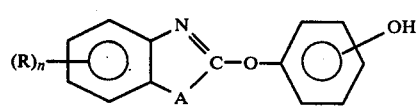

in which
R is an identical or different radical selected from the group of halogen, —$CF_3$, methyl and ethyl,
A is O, S, or N-($C_1$–$C_4$) alkyl and
n is zero to 2, and when R is —$NO_2$ or —CN, n is zero to 1, with the proviso that if n is zero and A is S, the free OH group does not stand in p-position to the ether linkage.